(12) United States Patent
Green et al.

(10) Patent No.: US 8,920,859 B2
(45) Date of Patent: Dec. 30, 2014

(54) STIGMASTEROL-RICH PHYTOSTEROL COMPOSITION AND USE

(75) Inventors: Daniel Albert Green, Media, PA (US); H. David Rosenfeld, Drumore, PA (US); Michael Jonathan Doby, Vienna, WV (US); Scott Winston, Welwyn Garden (GB); Harry Levine, Morris Plains, NJ (US); Louise Slade, Morris Plains, NJ (US); Dennis Brooks, Weston, NJ (US)

(73) Assignee: Diageo Great Britain Ltd., London (GB)

( * ) Notice: Subject to any disclaimer, the term of this patent is extended or adjusted under 35 U.S.C. 154(b) by 119 days.

(21) Appl. No.: 13/423,371

(22) Filed: Mar. 19, 2012

(65) Prior Publication Data

US 2013/0078358 A1  Mar. 28, 2013

Related U.S. Application Data

(60) Provisional application No. 61/454,711, filed on Mar. 21, 2011.

(51) Int. Cl.

| | | |
|---|---|---|
| *A23B 4/03* | (2006.01) | |
| *A23B 4/044* | (2006.01) | |
| *C07J 9/00* | (2006.01) | |
| *C07J 13/00* | (2006.01) | |
| *A23G 9/04* | (2006.01) | |
| *A23L 1/30* | (2006.01) | |
| *A23L 2/52* | (2006.01) | |
| *A23G 9/42* | (2006.01) | |
| *A23G 9/52* | (2006.01) | |
| *C07J 75/00* | (2006.01) | |

(52) U.S. Cl.
CPC ............... *C07J 13/00* (2013.01); *A23G 9/045* (2013.01); *A23L 1/3004* (2013.01); *A23L 2/52* (2013.01); *A23G 9/42* (2013.01); *A23G 9/52* (2013.01); *C07J 75/00* (2013.01)
USPC .......................................... 426/465; 552/544

(58) Field of Classification Search
USPC .......................................... 426/465; 552/544
See application file for complete search history.

(56) References Cited

U.S. PATENT DOCUMENTS

| | | | |
|---|---|---|---|
| 5,239,819 A | 8/1993 | Kinneberg | |
| 5,853,785 A | 12/1998 | Nayyar et al. | |

(Continued)

FOREIGN PATENT DOCUMENTS

| | | |
|---|---|---|
| EP | 1 142 494 A1 | 10/2001 |
| EP | 1 402 784 A1 | 3/2004 |

(Continued)

OTHER PUBLICATIONS

PCT International Search Report and Written Opinion mailed Jun. 22, 2012.

(Continued)

*Primary Examiner* — Humera Sheikh
*Assistant Examiner* — Tynesha McClain-Coleman
(74) *Attorney, Agent, or Firm* — Scherrer Patent & Trademark Law P.C.; Stephen T. Scherrer; Monique A. Morneault

(57) ABSTRACT

A stigmasterol-rich phytosterol composition is prepared wherein the composition comprises at least 50% stigmasterol, based on the total weight of phytosterols, no more than 1000 ppm water, no more than 50 ppm ethanol, and wherein stigmasterol is at least 98% in the anhydrous form. A ready-to-freeze beverage is provided comprising the stigmasterol-rich composition and water, with optional additives. A frozen beverage is prepared from the ready-to-freeze beverage as a pourable slush. There are further provided processes to prepare the ready-to-freeze beverage and the frozen slush beverage.

11 Claims, 1 Drawing Sheet

(56) References Cited

U.S. PATENT DOCUMENTS

2002/0183530 A1* 12/2002 Aaltonen et al. .............. 552/545
2006/0018866 A1   1/2006 Kawakami et al.

FOREIGN PATENT DOCUMENTS

| FR | 2828378 A1 | 2/2003 |
| WO | 96/11578 A1 | 4/1996 |
| WO | 2009/068651 A1 | 6/2009 |
| WO | 2010/146392 A1 | 12/2010 |

OTHER PUBLICATIONS

Fukuta et al., Epitaxial Growth of Ice on Organic Crystals, J. Phys. Chem. Solids, 1963, pp. 715-718, vol. 24, Pergamon Press, Great Britain.

R. B. Head, Ice Nucleation by Some Cyclic Compounds, J. Phys. Chem. Solids, 1962, pp. 1371-1378, vol. 23, Pergamon Press, Great Britain.

Xu et al., Separation and purification of stigmasterol and β-sitosterol from phytosterol mixtures by solvent crystallization method, Separation and Purification Technology, 2005, pp. 173-178, vol. 41.

Benavides et al., Stigmasteol hemihydrate, Crystal Structure Communications, Acta Crystallographica, 2002, pp. o131-o132, vol. C58.

Jiang et al., New Antiviral Cassane Furanoditerpenes from Caesalpinia minax, Journal of Natural Products, 2001, pp. 1266-1272, vol. 64.

* cited by examiner

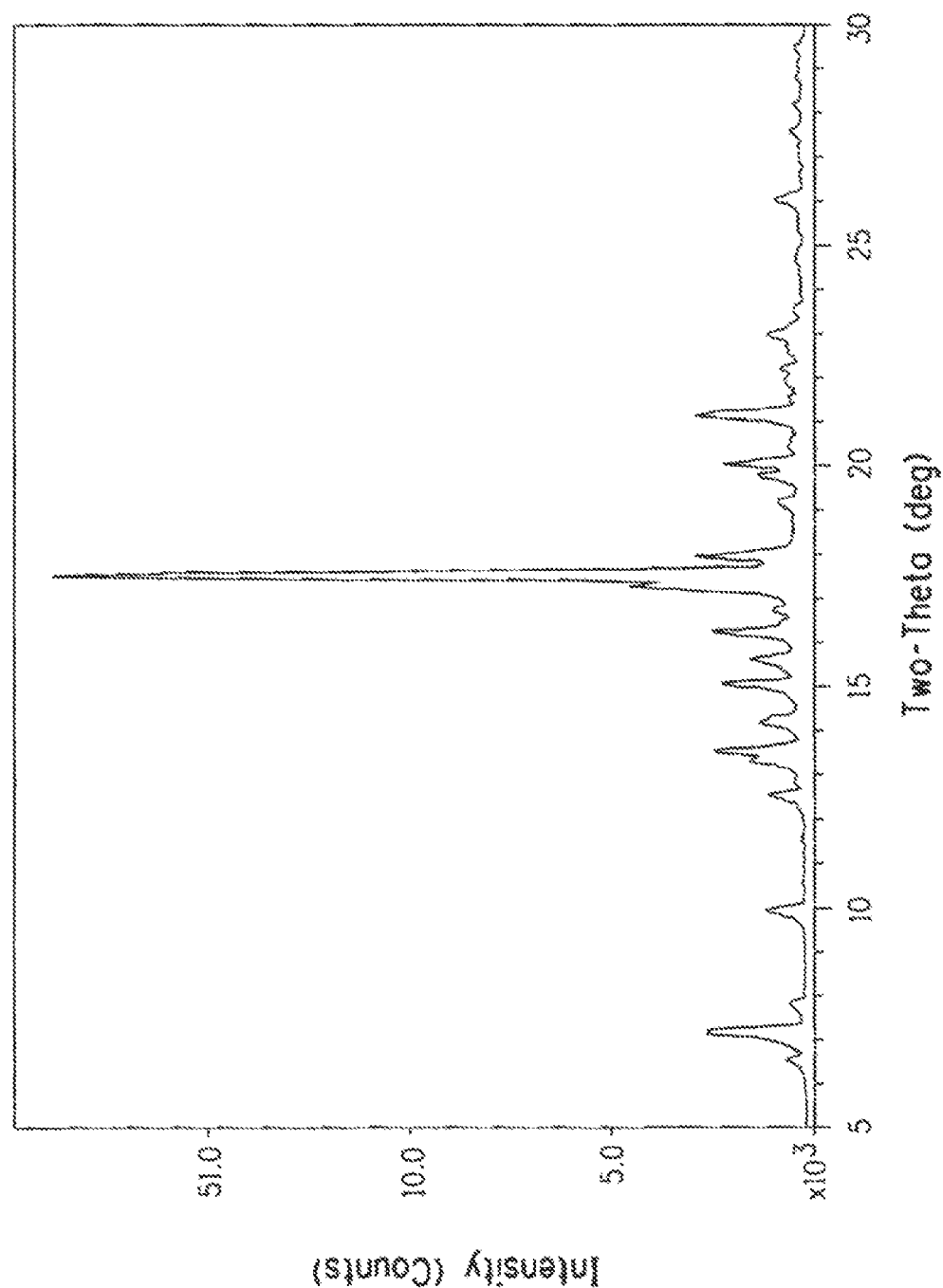

STIGMASTEROL-RICH PHYTOSTEROL COMPOSITION AND USE

FIELD OF THE INVENTION

The present invention pertains to the preparation of stigmasterol forms with improved reliability in ice nucleating applications and use of stigmasterol so prepared as an ice nucleating agent. In one example, such improved forms of stigmasterol are used in ready-to-freeze beverages. There is also provided a ready-to-freeze beverage comprising these improved forms of stigmasterol which reliably forms a semi-solid or slushy consistency upon freezing in a domestic freezer.

BACKGROUND OF THE INVENTION

Beverage slushes (drinkable liquid with a semi-solid or slushy consistency) are popular treats. Such beverages contain dispersions of ice in a liquid, which typically contains flavoring, sweetener, and other additives.

Methods and equipment are known to provide slush beverages in commercial and home environments. In commercial environments, such beverages may need to undergo constant mechanical agitation to prevent agglomeration of the ice crystals. At home or in food service industries, such beverages may be produced using blenders or other similar equipment just prior to consumption. Thus, preparation of slushy beverages requires suitable equipment and can be tedious or time-intensive, even if the necessary equipment is available.

Several products have been marketed recently to provide greater convenience, with the ability to freeze in a freezer, such as a static domestic freezer, and deliver a slush-type product. However, these products often suffer from disadvantages. Many products lack versatility to form the desired slush beverage over the range of domestic (home) freezer temperatures that are encountered. Problems encountered with these products include failure to form ice and formation of insufficient amounts of ice, which result in a cold beverage but no slushy consistency. Other products fail by over-hardening, resulting in a product that requires thawing before dispensing and/or consuming as a beverage.

Winston et al. in WO 2010/146392 disclose a slush beverage, which involves a balance of ingredients, with each ingredient having an effect on pourability of the product slush. The slush can be made using a domestic freezer or appropriate cooling apparatus. Winston et al. disclose preferably using an ice-nucleating agent (nucleator) to ensure ice formation in a domestic freezer. The preferred nucleator is stigmasterol, but the form and degree of hydration of the stigmasterol is not mentioned. While Winston et al. provide an advance in producing slush beverages in domestic environments, problems have been encountered by lack of consistent ice formation. Reliability of ice nucleation (failure rate) is an issue.

Commercially available stigmasterol exists in hydrated form, solvated form (ethanol solvent), and combinations thereof. The stigmasterol as-provided is unable to consistently maintain activity as an ice-nucleating agent in slush beverages upon common storage conditions, including time, temperature and relative humidity.

Kinneberg, in U.S. Pat. No. 5,239,819, discloses improved sterol nucleators of ice crystals. These sterols are specified to be 'terminally hydrated'. This crystal form was said to stable for long periods of time and provide predictable nucleation temperatures. The preparation of terminally hydrated stigmasterol was exemplified.

There still remains a need for improved ice nucleating agents which provide consistent freeze performance. In a practical application, it is desired to have an improved ice nucleating agent that may be used, for example, in ready-to-freeze beverages containing such agents which are liquid at ambient temperature and which consistently freeze over a range of temperatures as may be encountered in domestic and commercial freezers to form a pourable slush.

SUMMARY OF THE INVENTION

The present invention pertains to a process to prepare an anhydrous form of stigmasterol having improved ice-nucleating properties, and to the anhydrous stigmasterol composition thus prepared. The invention further pertains to a ready-to-freeze slush beverage comprising this anhydrous form of stigmasterol.

In one aspect there is provided a process comprising heating crude stigmasterol, which can be a crude stigmasterol-rich phytosterol blend, under conditions of time and temperature to reduce the amount of water and/or ethanol and/or to convert stigmasterol in amorphous and/or hydrated crystal form, to provide a stigmasterol-rich phytosterol composition comprising at least 50% stigmasterol, based on the total weight of phytosterols in the composition, no more than 1000 ppm water and no more than 50 ppm ethanol, wherein stigmasterol is at least 98% in the anhydrous form. For purposes herein, all measurements in ppm, or parts per million, are on a weight/weight basis. Commercial (crude) stigmasterol products typically contain water and sometimes ethanol due to the production processes wherein stigmasterol is extracted from various sources including plants. The process of the present invention reduces water and ethanol in the crude stigmasterol to very low levels.

In another aspect, there is provided a process to prepare an improved stigmasterol ice nucleating agent, said process comprising: providing a sample of crude stigmasterol having more than 1000 ppm water; heating said crude stigmasterol under conditions of time and temperature to convert substantially all of the crude stigmasterol to anhydrous stigmasterol having less than 1000 ppm water, or less than 750 ppm water, or less than 350 ppm water, or less than 100 ppm water or less than 50 ppm water.

In yet another aspect, there is provided an anhydrous stigmasterol composition produced according to these processes. It will be appreciated by those skilled in the art that the anhydrous stigmasterol composition, including the anhydrous stigmasterol-rich phytosterol composition, should meet requirements for use in food products when such use is contemplated.

The present invention further provides a process to prepare a ready-to-freeze beverage comprising (a) providing a stigmasterol-rich phytosterol composition comprising at least 50% stigmasterol, based on the total weight of phytosterols in the composition, no more than 1000 ppm water and no more than 50 ppm ethanol, wherein stigmasterol is at least 98% in the anhydrous form, prepared as described herein; and (b) contacting the stigmasterol composition provided in step (a) with water. Optionally one or more additives such as flavor, sweetener, and ethanol may be added in the contacting step (b).

The present invention further provides a pourable slush beverage that can be purchased in liquid form as a shelf-stable, ready-to-freeze beverage by a consumer. The ready-to-freeze beverage remains liquid at room temperature, is stable upon storage, and when placed in a domestic or other conventional freezer for a period of time, such as 6 hours, the liquid forms a frozen slush beverage. The ready-to-freeze beverage maintains its ability to form a frozen slush beverage after preparation, transportation, and storage in liquid form in retail outlets and home environments at a wide range of conditions.

The ready-to-freeze beverage can be stored at a temperature below the melting point of the beverage. As will be appreciated by one skilled in the art, the melting point of the beverage will vary depending on the beverage composition. The storage temperature is sufficient for ice to form in the beverage. Such temperature will be less than 0° C., preferably in the range of −11° C. to −20° C., most preferably −14 to −20° C. for a period sufficient to freeze the water in the beverage such that the liquid converts to a pourable slush, a drinkable frozen slush beverage. Such temperatures are typical of those in domestic and commercial freezers. The ready-to-freeze beverage comprises water and the stigmasterol-rich phytosterol composition which is disclosed herein, in particular, the stigmasterol composition prepared according to the process disclosed herein. Optionally, the beverage further comprises flavor, sweetener, ethanol, and combinations of two or more thereof.

It has been surprisingly found that a stigmasterol-rich phytosterol composition comprising stigmasterol in the anhydrous form, rather than a hydrated form, a solvated form, or combination of these forms, imparts reliability and reproducibility in ready-to-freeze beverages to form slush when cooled in typical freezers even if stored at temperatures above 50° C. and relative humidity greater than 97%.

There is further provided a process to prepare a frozen slush beverage comprising reducing the temperature of the ready-to-freeze liquid beverage to less than the melting point of the beverage, less than 0° C., for a period of time and under conditions as described hereinbelow sufficient to transform the liquid beverage into a slush.

BRIEF DESCRIPTION OF THE DRAWING

FIG. 1 shows an x-ray powder diffraction scan of anhydrous stigmasterol, prepared in accordance with Example 2.

DETAILED DESCRIPTION OF THE INVENTION

Stigmasterol is an unsaturated plant sterol occurring in plant fats such as soybean oil, rape seed oil and cocoa butter. It is commercially available form a variety of vendors such as, for example, Vita-Solar Biotechnology Co., Ltd, Xi'an, China.

Two crystalline forms of stigmasterol have been reported, a monohydrate and a hemihydrate. The three dimensional crystal structure of the monohydrate was disclosed by Ren-Wang Jiang, Shuang-Cheng Ma, Paul Pui-Hay But, and Thomas C. W. Mak in J. Nat. Prod. 2001, 64, 1266-1272. The unit cell parameters of the monohydrate are a=10.2679(10), b=7.6293(7), c=35.392(4) Å; beta=94.402(2)°; and the space group is monoclinic $P2_1$. The three dimensional crystal structure of the hemihydrate was disclosed by Gloria Benavides, Frank Fronczek, and Nicholaus Fischer in Acta Cryst. (2002), C58, 0131-0132. The unit cell parameters of the hemihydrate are a=9.523.2, b=7.5789.7, c=36.980.3 Å; beta=94.213(10)°; and the space group is monoclinic $P2_1$.

In the present invention, it has been found that the desired form of stigmasterol is a crystalline form which has not been previously reported. Therefore, as reported in the Examples hereinafter, the three-dimensional crystal structure has been solved. The unit cell parameters are: a=50.816(59) Å, b=7.240(61) Å; c=25.423(60) Å; B=113.807(43)°; and the space group is monoclinic C2. For convenience this crystal form is referred to as the "C2" form. The C2 form crystallized in a columnar morphology.

Standard X-ray powder diffraction (XRD) techniques distinguish the stigmasterol C2 form from the monohydrate and hemihydrate ("$P2_1$") forms. However, the crystal form alone, as determined by XRD, does not fully characterize the stigmasterol for the purposes of this invention. For example, the as-received commercial stigmasterol used in the Examples was substantially in the C2 crystal form. However, not until treatment according to the process of the present invention, wherein the moisture associated with the crystals is reduced to a very low level, does the stigmasterol take on superior reliability and stability properties in ice nucleating applications. While not wishing to be bound by theory, it appears possible for C2 stigmasterol to accommodate water (hydrated C2 form) in a way that changes physical attributes but does not perceptibly change the XRD.

It has been found that after heat treatment to reduce moisture content, for example below 1000 ppm water, the anhydrous stigmasterol crystals (which are in C2 form) become substantially non-hygroscopic (i.e., do not pick up atmospheric moisture) even in high humidity such as provided in a 97% relative humidity chamber. In contrast, a commercial sample of stigmasterol, also in the C2 form but having, for example, 4600 ppm associated water, is hygroscopic and picks up moisture readily on standing in similar high humidity conditions. Here again, there is a perceptible difference in physical attribute, hygroscopicity, which is not readily distinguishable in standard XRD analysis.

The stigmasterol prescribed in the present invention is thus referred to simply as "anhydrous stigmasterol". Each of the prescribed anhydrous stigmasterol and the prescribed anhydrous stigmasterol composition is characterized by water content of less than 1000 ppm water, and typically less than 750 ppm water and an ethanol content of less than 50 ppm ethanol, typically less than 30 ppm ethanol. In one embodiment, the moisture content of each of the anhydrous stigmasterol and the stigmasterol composition is less than 350 ppm. In another embodiment, the moisture content of each of the anhydrous stigmasterol and the stigmasterol composition is less than 100 ppm. In still another embodiment, the moisture content of each of the anhydrous stigmasterol and the stigmasterol composition is less than 50 ppm. The moisture content can be readily determined by standard Karl Fischer titration methods.

In another aspect, each of the anhydrous stigmasterol and the stigmasterol composition according to the present invention having less than 1000 ppm water is substantially non-hygroscopic. Thus, the moisture pickup of anhydrous stigmasterol or stigmasterol composition exposed to 97% relative humidity and 52° C. is substantially nil. By substantially nil it is meant that the moisture content increases no more than about 20 ppm water after one week of exposure to 97% relative humidity at 52° C. In one embodiment, the moisture content of anhydrous stigmasterol or stigmasterol composition starts at less than 750 ppm water and remains less than 750 ppm water after one week of exposure to 97% relative humidity at 52° C. In another embodiment, the moisture content of anhydrous stigmasterol or stigmasterol composition starts at less than 350 ppm water and remains less than 350 ppm water after one week of exposure to 97% relative humidity at 52° C. In still another embodiment, the moisture content of anhydrous stigmasterol or stigmasterol composition starts at less than 100 ppm water and remains less than 100 ppm after one week of exposure to 97% relative humidity at 52° C. In yet another embodiment, the moisture content of anhydrous stigmasterol or stigmasterol composition starts at less than 50 ppm water and remains less than 50 ppm after one week of exposure to 97% relative humidity at 52° C.

In forming the anhydrous stigmasterol or composition, the starting stigmasterol need not be in the hydrated C2 form as the $P2_1$ forms will also be converted to the desired anhydrous form by treatment according to the process of the present invention.

Commercially available stigmasterol may be a stigmasterol-rich phytosterol blend, or it may be relatively pure. In any case, the commercial stigmasterol, especially the food grade stigmasterol, usually comprises water and sometimes ethanol in amounts of at least 0.5% and commonly at least 1% weight or more. Such commercial stigmasterol may comprise any or a combination of crystal forms such as those described hereinabove. Regardless of percent (%) purity, for convenience, commercial stigmasterol comprising more than 1000 ppm water and optionally more than 30 ppm ethanol is referred to as "crude stigmasterol-rich phytosterol blend" or simply "crude stigmasterol". The crude stigmasterol can have more than 1100 ppm, more than 2000 ppm, more than 3000 ppm, or more than 4000 ppm water. Crude stigmasterol may be produced in ethanol, or recrystallized or precipitated using ethanol as a solvent. Crude stigmasterol may be prepared by other methods known to those skilled in the art.

Crude stigmasterol-rich phytosterol blends can act as ice nucleating agents, for example, in slush beverages, but performance is inconsistent and the effectiveness diminishes over time. It has been surprisingly found that converting crude stigmasterol to the anhydrous form as prescribed in the present invention provides consistent and stable effectiveness as an ice-nucleating agent.

Only a small amount of ice nucleating agent, maybe a few grains of solid anhydrous stigmasterol per container, is needed to achieve the desired performance. Therefore, to ensure consistent delivery of the requisite anhydrous stigmasterol crystals, it is advantageous that the stigmasterol-rich phytosterol is relatively high in stigmasterol content. The stigmasterol-rich phytosterols composition typically comprises at least 50% by weight stigmasterol, preferably at least 85% and more preferably at least 95% by weight of stigmasterol, based on the total weight of phytosterols in the composition. A stigmasterol-rich phytosterol composition may comprise 95 weight % stigmasterol and 5 weight % other plant sterols, based on the total plant sterol content of the composition. A stigmasterol-rich phytosterol composition may comprise 100 weight % stigmasterol based on the total plant sterol content of the composition. The presence of other plant sterols has not been found to negatively impact the ice-nucleating ability of stigmasterol. In cases where the crude stigmasterol comprises ethanol, preferably the anhydrous stigmasterol composition comprises no more than 30 ppm ethanol.

A preferred process to prepare the anhydrous stigmasterol composition prescribed by this invention comprises heating a crude stigmasterol-rich phytosterol blend under conditions of temperature, time, and pressure to remove water and/or ethanol from the blend and produce a product wherein at least 98% by weight of the stigmasterol present is in the anhydrous form. The product, an anhydrous stigmasterol-rich phytosterol composition, comprises no more than 1000 ppm water and no more than 50 ppm ethanol, preferably no more than 30 ppm ethanol.

In the heating process, time, temperature, and pressure are interdependent variables. For example, as will be appreciated by one skilled in the art, a higher temperature will require less time, and analogously, a lower temperature will require more time to remove water and/or ethanol and to form the anhydrous crystalline stigmasterol composition in this invention. Similarly, heating under vacuum will require less time than heating at the same temperature but under ambient pressure.

A suitable temperature at which to heat the crude stigmasterol may be at least 94° C. and preferably at least 112° C. Generally, when processing stigmasterol in powder form, the heating temperature will not exceed the melting point (about 168-170° C.) or any such temperature which causes the stigmasterol-rich phytosterol composition to decompose or discolor. As previously recited, time required for converting crude stigmasterol-rich phytosterols blends to the anhydrous stigmasterol composition of this invention depends on heating conditions. Selecting an appropriate heating time based on heating conditions can be readily determined based on disclosures herein without undue experimentation by a person having ordinary skill in the art.

Heating may occur in an oven, fluidized bed, tumble dryer, or by other means that can be readily ascertained by one skilled in the art. Heating may occur in the presence or absence of air (oxygen) or under vacuum, as indicated previously. The crude stigmasterol-rich phytosterol blend or crude stigmasterol is charged to a container such as a flask, tray or other container that fits the dimension of the oven or other equipment.

Stigmasterol-rich phytosterol compositions comprising at least 50% stigmasterol, based on the total weight of phytosterols, at least 98% stigmasterol in the anhydrous crystal form and comprising no more than 1000 ppm water and no more than 50 ppm ethanol, for use in the ready-to-freeze beverage of this invention can be prepared by recrystallizing crude stigmasterol-rich phytosterol blend from the molten state, such as at temperatures greater than about 168° C., for example, temperatures from about 168° C. to about 180° C.

The present invention provides a ready-to-freeze beverage that can be purchased and stored at room temperature and remain in liquid form. This beverage can be placed in a home or commercial freezer or other cooling equipment or reducing the temperature by other means, for example, to a temperature below the melting point of the beverage, less than 0° C., preferably in the range of −11° C. to −20° C., more preferably, −14° C. to −20° C. to form a pourable slush beverage that is ready for consumption.

An ice nucleating agent, anhydrous stigmasterol, is a component of the ready-to-freeze beverage. The anhydrous stigmasterol reliably initiates the freezing process and ensures that the beverage will freeze at temperatures typically encountered in domestic freezers. Ice nucleation is important to forming ice particles, otherwise a supercooled liquid persists which is not the desired product format.

The ready-to-freeze beverage of this invention freezes reliably to a slush even when, prior to freezing and use by the consumer, the beverage is exposed to weeks of high temperature (over 50° C.) and humidity as may be encountered during and after beverage manufacture and distribution. Thus the stigmasterol-rich phytosterol compositions can be used in the ready-to-freeze beverage of this invention with excellent performance and low failure rate. Failure of a ready-to-freeze beverage means failure to form a slush beverage upon cooling to a temperature below the melting point of the beverage, less than about 0° C., and may be evidenced by the beverage maintaining a liquid form. For a commercially viable consumer product, failure rate should be no more than 1% of the products tested.

The present invention provides a shelf-stable, ready-to-freeze liquid beverage. This beverage comprises water, optional components, and the stigmasterol-rich phytosterol composition which is disclosed herein, in particular, a stigmasterol-rich composition prepared according to the process disclosed herein. By "shelf-stable" is meant herein, the ready-to-freeze beverage of this invention forms a slush beverage upon freezing after a storage period at temperatures over 50° C. and under high humidity of a minimum of 6 weeks, with a rate of failure (as defined hereinabove) of less than 1%.

Freezing is defined herein as reducing the temperature of the beverage to a temperature below its melting point, less than 0° C., preferably in the range of −11° C. to −20° C., more preferably in the range −14° C. to −20° C.

The beverage may comprise one or more optional components such as flavor, sweetener, emulsifiers, food colors, acidulants, pH adjusting agents, and stabilizers, among others, as will be known to those skilled in the art.

An effective amount of ice nucleating agent, such as anhydrous stigmasterol, is that amount necessary to reliably induce ice nucleation in a finished product such as a slush beverage. An effective amount of anhydrous stigmasterol in a slush beverage is typically in the range of 0.005 to 0.1 g per liter. The beverage composition optionally further comprises 10-30% by weight of sweetener. The beverage composition optionally further comprises more than 0% up to 5% by weight of flavor. The beverage composition optionally further comprises 8-12% by weight ethanol (for alcohol-containing beverages). The beverage composition optionally further comprises a milk ingredient such as dairy cream. The balance of the beverage is water.

The amount of water in the beverage can vary and is typically between 80% to greater than 99% by weight, based on the total weight of the beverage. Preferably the amount of water is at least 85% by weight, based on the total weight of the beverage.

The present invention further comprises a process to prepare a ready-to-freeze beverage comprising (a) providing the stigmasterol-rich phytosterol composition which is disclosed herein, in particular, a stigmasterol-rich composition prepared according to the process disclosed herein; and (b) contacting the stigmasterol-rich composition with water. The beverage preparation process optionally further comprises adding one or more of flavor, sweetener, ethanol, food color, acidulant, pH adjusting agent, and stabilizer. Preferably, the beverage preparation process further comprises adding one or more of flavor, sweetener and/or ethanol. Such preparations are disclosed, for example, in Winston et al. hereinbefore referenced. Where the beverage is intended for human consumption, the ingredients should be food-grade.

The amounts of stigmasterol-rich composition and water in addition to other components, such as flavor, sweetener, ethanol, and other additives are as set forth above. The contacting step can be performed at ambient, elevated or low temperature. The contacting step may be performed under ambient conditions (room temperature and pressure).

Also contemplated herein is a frozen slush beverage comprising ice crystals, stigmasterol-rich phytosterol composition, and optional additives.

The frozen slush beverage is prepared by placing the ready-to-freeze beverage in a freezer or otherwise reducing temperature to below the melting point of the beverage, that is, less than 0° C., preferably to a temperature of −11° C. to −20° C., more preferably to a temperature of −14° C. to −20° C.

In the present invention, it has been found that heat treating crude stigmasterol-rich phytosterol blends, produces an anhydrous stigmasterol-rich phytosterol composition that maintains its ice nucleation ability throughout production and storage at elevated temperatures. It will be appreciated by one having ordinary skill in the art that in forming the anhydrous stigmasterol, more or less time may be necessary as temperature, time, pressure and other conditions vary. Heat treatment under vacuum and at ambient pressure are both effective. After heat treatment, residual water content and ethanol content of the heat treated product—anhydrous stigmasterol or anhydrous stigmasterol-rich composition, are very low, no more than 1000 ppm water, no more than 50 ppm ethanol and stigmasterol is at least 98% in the anhydrous crystal form.

The ready-to-freeze beverage comprising the anhydrous stigmasterol-rich phytosterol composition provides less than 1% failures (to form slush) upon exposure to freezing at temperatures typical of domestic freezers. This compares favorably with and is advantageous compared to non-treated stigmasterol which suffers a much higher failure rate. Many flavors of slush beverage, both alcoholic and non-alcoholic, can be produced with the anhydrous stigmasterol of the present invention.

The process of this invention can be used to prepare the stigmasterol composition with the improved properties described hereinabove for use in various applications.

For example, a second application is for providing shelf-stable (where shelf-stable is described hereinabove) flavored water compositions, which, upon cooling to a temperature of −11° C. to −20° C., more preferably to a temperature of −14° C. to −20° C., freeze into a soft water ice form. Thus, products could be shipped and stored as liquids, exposed to heat and humidity and yet retain the ability to freeze in a desirable form.

Still further, the stigmasterol composition as prepared herein can be used in other applications which use ice nucleants. Such applications are frequent in the food and pharmaceutical industries, in particular, for products in which freeze-drying is applied (vitamins, nutrients, drugs, vaccines). Adding the food-grade stigmasterol composition as prepared herein as an additive to water sprayed on plants, such as fruit trees and vegetable crops, during cold weather conditions, may protect such plants from damage when temperatures are near or below 0° C., such as frost.

Even still further, other applications of the stigmasterol composition as prepared herein can be contemplated. For example, as a component of an ice slurry coolant system that requires ice particles to be formed.

EXAMPLES

Analytical Methods

The quantitative analysis of ethanol in stigmasterol-rich compositions is based on the GC/MS analysis of sample headspace in a closed vial heated at 125° C. for 15 minutes. Typically, a small amount of sample (~42 mg) was placed into a 10 mL headspace vial, then closed with a septum lid, and heated to the desired temperature (125° C.) to drive ethanol into the headspace. After the sample was heated for 15 minutes, the septum was pierced with a gas syringe and 1.0 cc of gas was withdrawn from the vial. The sample gas was injected into the gas chromatograph (GC) and then detected using a Mass Selective Detector (MSD). A calibration curve was prepared in one of two ways. For high level ethanol, 1 to 3 µL (where 1000 µL=1 mL) of pure ethanol was injected separately into a vial and then analyzed by headspace GC/MS as noted above. For low level ethanol, selected volumes (1 to 3 µL) of a 2.5 wt % ethanol solution in water were analyzed. Using the volume injected and the solution density (g/mL), the weight (mg) of standard solution in the headspace vial was calculated. The actual amount of ethanol (mg) was calculated using the standard solution weight (mg) in the vial and ethanol weight fraction (0.025). Ethanol and water were separated on a HP-5 ms column (30 m×0.25 mm×1 μm). The GC conditions included an inlet at 200° C., split ratio of 50:1, and helium flow rate of 1.2 mL/min at constant flow. Finally, the temperature program used was 40° C. held for 5 minutes, then ramped at 20° C. per minute to 220° C. and held for 5 minutes.

The quantitative analysis of water in stigmasterol-rich phytosterol compositions was performed using the Karl Fischer method of analysis.

X-ray powder data was obtained from a Philips X'PERT automated powder diffractometer, Model 3040. The diffractometer was equipped with automatic variable anti-scatter and divergence slits, X'Celerator RTMS detector, and Ni filter. The radiation was CuK(alpha) (45 kV, 40 mA). Data were collected at room temperature from 4 to 80 deg 2-theta; using a continuous scan with an equivalent step size of 0.02 deg; and a count time of 80 seconds per step in theta-theta geometry. Samples were ground with an agate mortar and pestle as needed and prepared on low background amorphous silica specimen holders as a thin layer of powdered material.

Example 1

Preparation of Anhydrous Stigmasterol from Crude Stigmasterol

A Thermo Electron Corporation VT 6025 vacuum oven was set to a temperature of 135° C. to achieve the desired solvent (water and ethanol) specifications. Crude stigmasterol (20 g, Vita-Solar Biotechnology Co., Inc., Xi'an, China) was placed in a 500-ml glass beaker. The beaker was transferred to an oven. The beaker remained in the oven for no longer than 4 days at a pressure of no more than 20 mbar (Edwards no. 12 Vacuum pump).

Analysis of the stigmasterol product removed from the oven showed the water and ethanol specifications of less than 1000 ppm water and less than 50 ppm ethanol were achieved.

Example 2

Alternative Preparation of Anhydrous Stigmasterol from Crude Stigmasterol

A Salvis Thermocentre oven was set at a temperature of 135° C., with an air feed set to the minimal opening so as to allow sufficient air exchange in the oven but to limit the presence of oxygen. A tray was charged with 100 g crude stigmasterol (from Vita-Solar Biotechnology Co., Inc.). The tray remained in the oven for no longer than 90 minutes at 135° C. Analysis of the stigmasterol product removed from the oven showed the water and ethanol specifications of less than 1000 ppm water and less than 50 ppm ethanol were achieved.

Example 3

Hygroscopicity and ice nucleating performance of anhydrous stigmasterol versus crude stigmasterol.

An aluminum tray containing 60 g of crude stigmasterol (from Vita-Solar Biotechnology Co., Inc.) was placed in an oven for four days at 135° C. to produce a stigmasterol composition having at least 98% stigmasterol in the C2 form as determined by X-ray diffraction, and less than 5 ppm water and less than 30 ppm ethanol (anhydrous stigmasterol, as prescribed). The tray containing the anhydrous stigmasterol and a similar tray containing a sample of crude stigmasterol (60 g, control, as received) were placed in a glass desiccator. The desiccator had been previously prepared with 120 g of potassium sulfate and 1 liter of water to provide an atmosphere of 97% relative humidity. The desiccator was then placed into an oven at 52° C. The trays were kept in the desiccator for 14 days.

Each day, a 3 g sample was removed from each tray in the desiccator. The 3 g samples that were removed after days 0 (before placing in 52° C. oven), 2, 4, 7 and 14 were analyzed for moisture content using Karl Fischer moisture content analysis. Results are shown in Table 1. Samples of anhydrous stigmasterol prepared in this Example 3 showed substantially no moisture pick up. In contrast, the crude stigmasterol samples removed from the desiccator (control stigmasterol) absorbed a substantial amount of water from the high humidity environment inside the desiccator.

TABLE 1

| Water, % | Day 0 | Day 2 | Day 4 | Day 7 | Day 14 |
|---|---|---|---|---|---|
| Crude Stigmasterol | 0.4627 | 0.6591 | 0.9453 | 1.15 | 1.45 |
| Anhydrous Stigmasterol | 0.000503 | 0.000553 | 0.000506 | 0.000731 | 0.000661 |

The ice nucleating performance of these samples was tested. An ethanol stock solution of 16% by weight ethanol in deionized water solution was prepared by adding 200 mL of ethanol to 1050 mL of deionized water. Into each of 8-100 mL bottles was placed 50 mL of the ethanol stock solution. Portions of the 3-g samples removed from the trays in the desiccator were tested for freeze performance in the stock solution. A 30-mg sample of the anhydrous stigmasterol from day 1 was added to 4 bottles and a 30-mg sample of control stigmasterol from day 1 was added to the other 4 bottles. That is, 4 samples were taken for each day, to have 4 runs per sample. All 8 bottles were then placed in a freezer at −14° C. The following day (after 24 hours), all of the bottles were removed from the freezer to check for "Pass" or "Fail". The sample in the bottle was rated a Pass if there was any ice present in the bottle. If no ice was present, the sample was rated a Fail. All day 1 samples passed.

A similar process was followed for days 2-14, with samples being taken and 4 runs for each sample. Results are provided in Table 2 for days 4, 7, and 10.

TABLE 2

| Anhydrous Stigmasterol | | | | Control (crude stigmasterol) | | | |
|---|---|---|---|---|---|---|---|
| Run # | Day 4 | Day 7 | Day 10 | Run # | Day 4 | Day 7 | Day 10 |
| 1 | Pass | Pass | Pass | 1 | Fail | Pass | Pass |
| 2 | Pass | Pass | Pass | 2 | Pass | Fail | Pass |
| 3 | Pass | Pass | Pass | 3 | Fail | Pass | Pass |
| 4 | Pass | Pass | Pass | 4 | Fail | Pass | Pass |

As shown in Table 2, the heated-treated anhydrous stigmasterol samples passed on every analysis whereas some of the control crude stigmasterol samples failed. A failure rate of 33% as illustrated for the control crude stigmasterol is unacceptable for a consumer-directed product.

Example 4

Crude stigmasterol was placed in an oven for four days at 135° C. to produce an anhydrous stigmasterol composition. The stigmasterol composition and a crude (as-received) stigmasterol sample (Control) were both exposed to 97% relative humidity at 52° C. for 4, 7 and 10 days similar to the process of Example 3. A slush beverage formulation containing ethanol (96.4%) 134.8 mL (105 g); emulsion (dairy cream concentrate) 25 mL; sucrose 240 g; gelatin 50 g; chocolate flavors, 3 mL; and demineralized water to 1000 mL total volume, was prepared. Into each of twenty-four 100 mL bottles were placed 50 mL of the liquid beverage and 30 mg of anhydrous stigmasterol crystals. These 24 bottles along with 24 similarly prepared bottles containing crude stigmasterol instead of the anhydrous were all placed in the 52° C. oven. Each of the 48 bottles was kept sealed and maintained in the 52° C. oven for 4 days.

The 48 bottles were removed from the oven and allowed to cool to room temperature. After a few hours, all 48 bottles were then placed into a freezer overnight (−11° C.). Results for the samples (4 runs each) in the formulation are provided in Table 3.

TABLE 3

| Anhydrous Stigmasterol | | | | Control (crude stigmasterol) | | | |
|---|---|---|---|---|---|---|---|
| Run # | Day 4 | Day 7 | Day 10 | Run # | Day 4 | Day 7 | Day 10 |
| 1 | Pass | Pass | Pass | 1 | Pass | Pass | Pass |
| 2 | Pass | Pass | Pass | 2 | Pass | Pass | Fail |
| 3 | Pass | Pass | Pass | 3 | Fail | Pass | Pass |
| 4 | Pass | Pass | Pass | 4 | Fail | Pass | Fail |

As shown in Table 3, the samples with the prescribed anhydrous stigmasterol passed on every analysis whereas the control crude stigmasterol samples again had a 33% failure rate.

Example 5

Three different samples of stigmasterol were compared. The first sample (Control) was crude stigmasterol as received from Vita-Solar. The second sample (Comparative) was "terminally hydrated" stigmasterol produced by the method of Kinneberg in U.S. Pat. No. 5,239,819, Example C. The third sample was anhydrous stigmasterol according to the present invention, prepared from the crude Vita-Solar stigmasterol by heat-treatment at 135° C. under inert atmosphere for a period of 90 minutes. The three different stigmasterol samples were analyzed and the results are set forth in Table 4.

TABLE 4

| Specification | Crude Stigmasterol (Control) | Terminally Hydrated Stigmasterol (Comparative) | Anhydrous Stigmasterol |
|---|---|---|---|
| Water Content (%) | 1.5 | 5.2 | 0.07 |
| Residual Ethanol (%) | 0.5 | 3 | <0.001 |
| Melting Point (° C.) | 162 | 170 | 168 |
| Stigmasterol (%) | 92 | 93 | 92 |

All three stigmasterol materials were separately stored, for a period of 4 months after production, in an air-tight storage container at ambient temperature, and then tested for ice-nucleation activity.

Bottles of slush beverage were prepared with the following general formulation: ethanol (96.4%) 145.2 mL; fructose, 140 g; glucose, 40 g; gelatin, 20 g; maltodextrin 10 g; citric acid, 6 g; citrus flavors, 5 mL; and demineralized water to 1000 mL. Each bottle was charged with 100 mL of beverage and 30 mg of stigmasterol which was either crude, terminally hydrated or anhydrous stigmasterol. A total of eighty bottles with each of the three stigmasterol samples was prepared and tightly sealed. A set of eighty bottles with no stigmasterol was also prepared as control samples.

All bottles were placed in a 52° C. oven to simulate the high-temperature conditions that the beverage could experience during transportation and storage in the hot summer months. After 4 days, forty bottles of each stigmasterol and control were removed from the oven and tested for freeze performance by placing them in a laboratory freezer at −14° C. for 24 hours. The number of bottles frozen after 24 hours was counted. The remainder of the bottles were kept in the oven for 14 days, after which time they were removed and tested for freeze performance in a similar manner.

The freeze performance results are summarized in Table 5. A reported value of 30%, for example, means that only 12 of the 40 bottles in that set of samples froze. Most preferably, 100% of the samples would freeze. The results show the vastly superior performance of the anhydrous stigmasterol prescribed in the present invention relative to Controls with no stigmasterol or with crude stigmasterol (as-received), and relative to Comparative terminally-hydrated stigmasterol.

TABLE 5

| Stigmasterol Type | % Samples frozen after 4 days, 52° C. | % Samples frozen after 14 days, 52° C. |
|---|---|---|
| Control—No Stigmasterol | 10% | 10% |
| Control—Crude Stigmasterol | 50% | 15% |
| Comparative—Terminally Hydrated Stigmasterol | 30% | 5% |
| Anhydrous Stigmasterol | 100% | 100% |

To follow up on the above results, a sample of the terminally hydrated stigmasterol (Comparative) was subjected to heating at 135° C. under an inert atmosphere for 1.5 hours to form anhydrous stigmasterol as prescribed. The anhydrous stigmasterol thus made was then tested as a nucleating agent in a slush beverage according to the procedure described in this example. All of these samples (100%) froze when placed in a freezer at −14° C., thus demonstrating that the terminally hydrated form of stigmasterol can be used as a starting material for forming anhydrous stigmasterol.

Example 6

The anhydrous stigmasterol prescribed by the present invention, as prepared in accordance with Example 2 hereinabove, is a crystalline powder which forms in the monoclinic space group C2 with unit cell parameters a=50.816(59) Å; b=7.240(61) Å; c=25.423(60) Å; and B=113.807(43)°. These parameters were determined as a result of single crystal X-ray diffraction analysis of a single crystal grown by sublimation. As this crystalline form is previously unreported, the crystallographic data (excluding structure factors) will be deposited with the Cambridge Crystallographic Data Centre (CCDC). Copies of the data will be available on application to CCDC, 12 Union Road, Cambridge CB2 1EZ, UK, (fax: +44 1223 336033 or e-mail: deposit@ccdc.cam.ac.uk).

The computer software package Jade v9.1.1 (copyright 1995-2012 Materials Data Inc.) was used to calculate the x-ray powder pattern of the single crystal from the space group, lattice constants and atomic positions. The calculated powder pattern of the single crystal matched the actual powder pattern of bulk anhydrous stigmasterol depicted in the FIG. 1, thus confirming their crystalline identity.

Table 6 summarizes the x-ray powder diffraction peaks of anhydrous stigmasterol as depicted in the FIG. 1 for those peaks with a relative intensity greater than ten (10).

TABLE 6

| 2-Theta (Cu kα) | d(Å) | (h, k, l) | Relative Intensity (%) |
|---|---|---|---|
| 3.798 | 23.2461 | (2, 0, 0) | 27.1 |
| 6.991 | 12.6347 | (−4, 0, 1) | 11.6 |
| 12.362 | 7.154 | (1, 1, 0) | 27.5 |
| 13.161 | 6.7216 | (1, 1, 1) | 29 |
| 13.373 | 6.6156 | (−3, 1, 1) | 14 |
| 14.924 | 5.9313 | (1, 1, 2) | 30.8 |
| 15.48 | 5.7194 | (−5, 1, 2) | 22.5 |
| 15.499 | 5.7127 | (5, 1, 0) | 11 |
| 16.087 | 5.5052 | (4, 0, 3) | 12.5 |
| 16.598 | 5.3367 | (3, 1, 2) | 12.4 |
| 17.133 | 5.1711 | (2, 0, 4) | 32.4 |
| 17.356 | 5.1052 | (−7, 1, 1) | 18.8 |
| 17.367 | 5.1022 | (1, 1, 3) | 15.7 |
| 17.429 | 5.0841 | (−7, 1, 2) | 15.5 |
| 17.438 | 5.0816 | (−10, 0, 2) | 100 |
| 17.836 | 4.9689 | (−10, 0, 3) | 11.2 |
| 19.937 | 4.4497 | (−9, 1, 2) | 37.8 |
| 22.832 | 3.8918 | (−11, 1, 2) | 19.8 |

What is claimed is:

1. A process to prepare an improved stigmasterol ice nucleating agent, said process comprising: providing a sample of crude stigmasterol having more than 1000 ppm water; heating said crude stigmasterol under conditions of time and temperature sufficient to form a composition having less than 1000 ppm water, wherein in said composition substantially all of the crude stigmasterol is converted to anhydrous crystalline stigmasterol, wherein the anhydrous crystalline stigmasterol is in the monoclinic space group C2 having unit cell parameters a=50.816(59) Å, b=7.240(61) Å, c=25.423(60) Å, and $\beta$=113.807(43)°.

2. The process of claim 1 wherein the heating is performed in an oven, fluidized bed or a tumble dryer.

3. The process of claim 1 wherein the condition of temperature is above about 94° C.

4. The process of claim 1 wherein the conditions of time and temperature are about 90 minutes and about 135° C., respectively.

5. An anhydrous stigmasterol composition prepared according to the process of claim 1.

6. The anhydrous stigmasterol composition of claim 5 having no more than 100 ppm water.

7. The anhydrous stigmasterol composition of claim 5 further characterized by a moisture pick up which is substantially nil at 97% relative humidity and 52° C.

8. The anhydrous stigmasterol composition of claim 5 wherein the anhydrous stigmasterol composition is food grade suitable for human consumption.

9. A frozen slush beverage comprising an effective amount of ice nucleating agent, wherein said ice nucleating agent comprises the anhydrous stigmasterol composition of claim 8.

10. The process of claim 1 wherein said heating of said crude stigmasterol is performed at about 1 atm or less.

11. The process of claim 1 wherein at least 98% of the crude stigmasterol is converted to the anhydrous crystalline stigmasterol.

* * * * *